United States Patent [19]

Shutt et al.

[11] Patent Number: 5,507,772
[45] Date of Patent: Apr. 16, 1996

[54] CLEANABLE, INSPECTABLE, AND REPLACEABLE SURGICAL INSTRUMENT

[75] Inventors: George V. Shutt, Glendora; Jeffrey G. Shutt, Running Springs, both of Calif.

[73] Assignee: DePuy Inc., Warsaw, Ind.

[21] Appl. No.: 247,020

[22] Filed: May 20, 1994

Related U.S. Application Data

[63] Continuation-in-part of Ser. No. 67,784, May 25, 1993, abandoned.

[51] Int. Cl.⁶ ..................................................... A61B 17/28
[52] U.S. Cl. ............................. 606/205; 606/207; 606/41
[58] Field of Search ..................................... 606/205–209, 606/45–52, 170, 171; 128/751, 752

[56] References Cited

U.S. PATENT DOCUMENTS

| | | |
|---|---|---|
| Re. 31,289 | 6/1983 | Moore et al. . |
| Re. 31,290 | 6/1983 | Moore et al. . |
| D. 345,212 | 3/1994 | Brancel et al. . |
| 984,756 | 2/1911 | Frisch . |
| 3,585,985 | 6/1971 | Gould . |
| 3,792,701 | 2/1974 | Kloz et al. . |
| 3,814,102 | 6/1974 | Thal . |
| 3,871,365 | 3/1975 | Chikama . |
| 3,915,157 | 10/1975 | Mitsui . |
| 3,924,608 | 12/1975 | Mitsui . |
| 4,043,343 | 8/1977 | Williams . |
| 4,122,856 | 10/1978 | Mosior et al. . |
| 4,201,213 | 5/1980 | Townsend . |
| 4,243,047 | 1/1981 | Olsen . |
| 4,369,788 | 1/1983 | Goald . |
| 4,573,450 | 3/1986 | Arakawa . |
| 4,574,803 | 3/1986 | Storz . |
| 4,590,936 | 5/1986 | Straub et al. . |
| 4,655,216 | 4/1987 | Tischer . |
| 4,662,371 | 5/1987 | Whipple et al. . |
| 4,706,656 | 11/1987 | Kuboto . |
| 4,712,545 | 12/1987 | Honkanen . |
| 4,763,669 | 8/1988 | Jaeger . |
| 4,782,819 | 11/1988 | Adair . |
| 4,836,205 | 6/1989 | Barrett . |
| 4,896,678 | 1/1990 | Ogawa . |
| 4,971,035 | 11/1990 | Ito . |
| 4,971,067 | 11/1990 | Bolduc et al. . |
| 4,977,900 | 12/1990 | Fehling et al. . |
| 5,026,375 | 6/1991 | Linovitz et al. . |
| 5,133,735 | 7/1992 | Slater et al. . |
| 5,133,736 | 7/1992 | Bales, Jr. et al. . |
| 5,141,519 | 8/1992 | Smith et al. . |

(List continued on next page.)

*Primary Examiner*—Stephen C. Pellegrino
*Assistant Examiner*—Michael Peffley
*Attorney, Agent, or Firm*—Barnes & Thornburg

[57] ABSTRACT

A surgical instrument includes a removable tip assembly having an elongated support member including a proximal end configured to be coupled to the handle and a distal end for insertion into a patient's body. The support member may either be straight or curved. The tip assembly also includes an operating unit coupled to the distal end of the support member, and a drive actuator having a distal end and a proximal end. The distal end of the drive actuator is pivotably coupled to the operating unit for moving the operating unit relative to the support member. The surgical instrument also includes a handle having a body portion formed to include an opening for receiving the proximal end of the tip assembly therein, a movable trigger configured to actuate the operating unit of the selected tip assembly, and a locking mechanism for removably coupling the selected tip assembly to the handle. The locking mechanism is movable from a first position to hold the selected tip assembly in a locked position relative to the handle to a second position to release the selected tip assembly from the handle and permit the removal of the selected tip assembly from the handle. The drive actuator can be rotated out of a slot in the handle while the tip assembly is assembled to the handle for cleaning, sterilization, and inspection. The support member, drive actuator, and operating unit cannot be disassembled from each other. Advantageously, the tip assembly may be removed and replaced. This permits replacement of a damaged tip assembly on site.

35 Claims, 5 Drawing Sheets

U.S. PATENT DOCUMENTS

| | | |
|---|---|---|
| 5,152,778 | 10/1992 | Bales, Jr. et al. . |
| 5,156,633 | 10/1992 | Smith . |
| 5,160,343 | 11/1992 | Brancel et al. . |
| 5,171,256 | 12/1992 | Smith et al. . |
| 5,171,258 | 12/1992 | Bales et al. . |
| 5,176,695 | 1/1993 | Dulebohn . |
| 5,176,699 | 1/1993 | Markham . |
| 5,192,298 | 3/1993 | Smith et al. . |
| 5,196,023 | 3/1993 | Martin . |
| 5,201,752 | 4/1993 | Brown et al. . |
| 5,201,759 | 4/1993 | Ferzli . |
| 5,203,785 | 4/1993 | Slater . |
| 5,344,428 | 9/1994 | Griffiths . |
| 5,391,180 | 2/1995 | Tovey et al. . |
| 5,392,789 | 2/1995 | Slater et al. . |

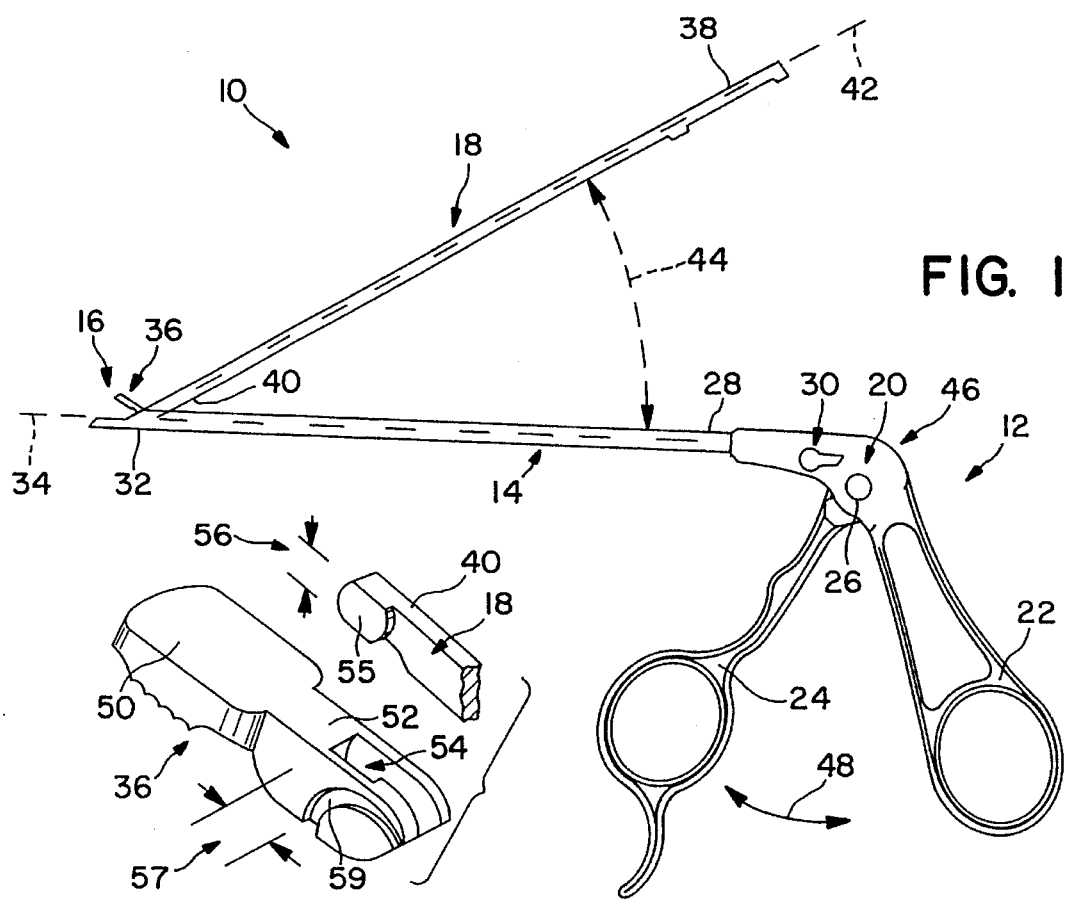
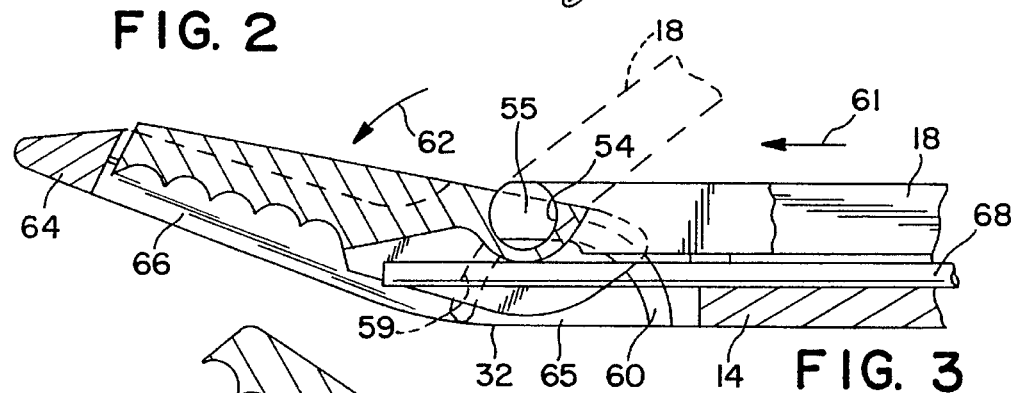
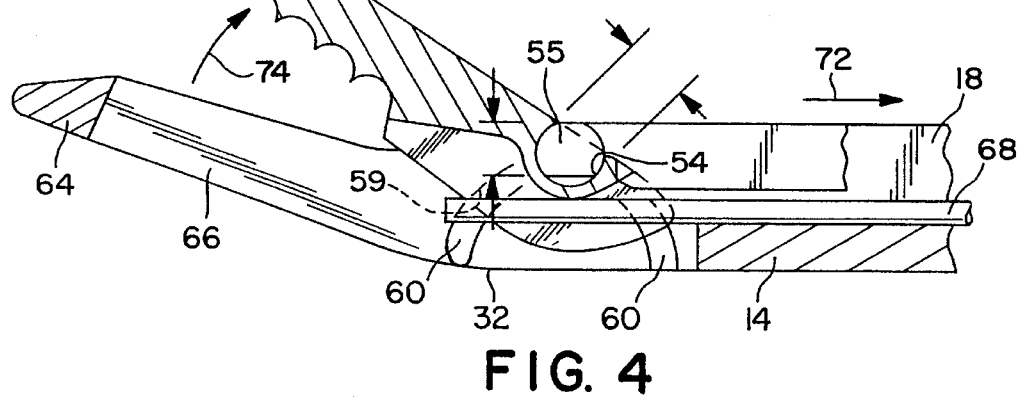

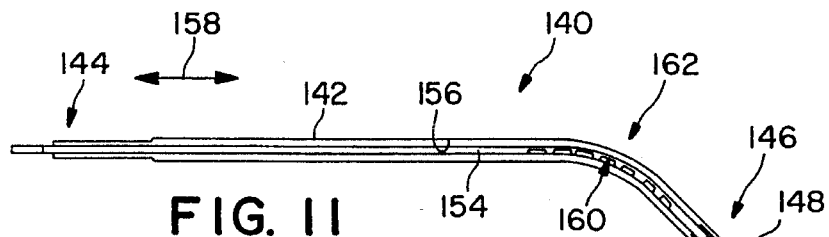
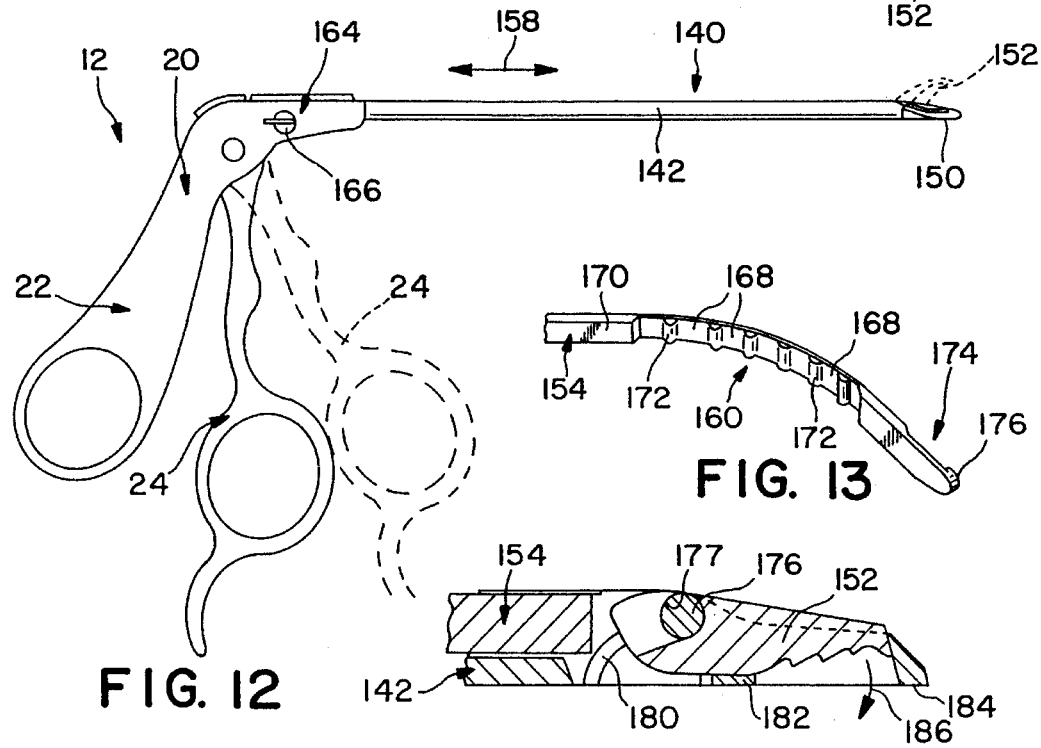
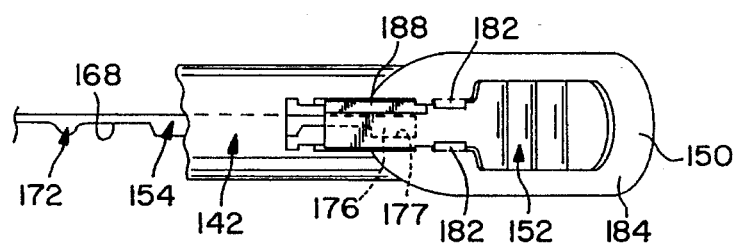

CLEANABLE, INSPECTABLE, AND REPLACEABLE SURGICAL INSTRUMENT

This application is a continuation-in-part of application Ser. No. 08/067,784 filed May 25, 1993, now abandoned.

BACKGROUND AND SUMMARY OF THE INVENTION

The present invention relates to surgical instruments and more particularly to the provision of Minimally Invasive Surgery (MIS) surgical instruments which are easily separable or the parts of which are releasably separable for cleaning and sterilizing and repair or replacement.

Various types of MIS surgery are now being performed by surgeons including laparoscopy, endoscopy and arthroscopy surgery. Surgical instruments usable in MIS surgery very commonly have a proximal end to be disposed outside the patient's body, a distal end to be disposed inside the patient's body and a support shaft or a barrel portion extending between the proximal end and the distal end. A handle mechanism or handle portion is disposed at or adjacent the proximal end of the instrument to provide means for gripping and manipulating the instrument. Typically, the handle portion will include a base handle grippable by the surgeon to hold and manipulate the instrument and a movable handle or trigger also manipulable by the surgeon, usually by a digit of the same hand that holds the base handle.

Various types of operating units are placed on the distal end of the instrument including scissors, various types of cutters, graspers, staple applicators, clip applicators, laser devices, viewing (optical) devices, illuminating devices, and any combination of these. In this specification, and in the appended claims, the term "operating unit" which is said to be mounted on the distal end of the instrument is some sort of unit for affecting and/or viewing tissue within the patient's body. Such operating units conventionally have at least one movable member, and some have two or more movable members. Essentially, the at least one movable member is the action member which, when moved relative to the shaft portion or barrel of the instrument, will cooperate with a stationary member somehow to affect or view the tissue of the patient's body. For instance, the at least one movable member may be a scissors blade, a grasper jaw, a staple driver, etc. The movable member may also be a lens of a fiber optic viewing system.

Conventionally, MIS instruments of the type described include a drive actuator or a drive member which extends along the barrel portion or support shaft to move rectilinearly or rotatably to move the at least one movable member of the operating unit. This drive actuator typically will be driven rectilinearly along the support shaft or barrel portion by pivotal or swinging movement of the movable handle or trigger of the handle mechanism at the proximal end of the instrument. The actuator may also be rotated about its axis relative to the support shaft to move at least one movable member.

Such MIS surgery instruments are very well known. Currently, many of such instruments are made to be disposable or intended for single use. In order to be used in MIS surgery, these instruments must be rather small and the parts thereof must be rather confined within the small diameter of the support shaft or barrel portion. Many of these instruments are used in rather small incisions or rather small cannulae or trocars extending into joints or through the abdominal wall of a patient. The basic concept behind MIS applications is to make rather small incisions or openings, typically 3 to 5 to 11 mm, in the patient to accommodate the operating or viewing units at the distal end of the instruments.

It is very expensive to dispose of these MIS instruments after a single patient use. The units are expensive and the disposal processes are expensive. Further, there are environmental problems associated with taking such disposable instruments to landfills and other disposal sites and systems. Another problem with single use or disposable instruments is that some hospitals and staff members are known to reuse them after at least an effort to sterilize them.

Sterilizing and cleaning these very small instruments, even if such an activity is attempted, is rather problematical using instruments of the prior art designs. Currently there are no cleaning devices to forcibly flush the body fluids and tissues, sometimes referred to as "bioburden", out of such narrow and confined spaces within MIS instruments after surgery. It is a matter of serious concern to surgeons that such cleaning activities be effective to clean and to sterilize the instruments. If toxic chemicals and/or gases are used in an attempt to clean and sterilize the instruments, there is always the possibility that such chemicals or gases will be trapped in the instruments to escape during surgery exposing both the patient and the health care professionals.

Recent clinical research has shown that tuberculosis, HIV, and some forms of hepatitis, in particular, are capable of surviving common sterilization methods, possibly to allow cross-contamination between patients or transmission to health care workers. It is reported that in 1991, about 200 health care workers died from hepatitis and nearly 9,000 health care workers were exposed to it.

While there are reusable MIS instruments and health care establishments are attempting to clean and sterilize them after each use, the operating units at the distal ends and the barrel portions or support shaft portions are very difficult to clean simply by soaking in chemicals and/or by autoclaving. In order to save on cost per patient and minimize environmental problems, MIS instruments need to be developed which can be thoroughly and easily cleaned, sterilized, and which can be reliably inspected after each surgery application.

The present invention, therefore, contemplates providing MIS instruments in which at least the portions of the instrument which are inserted within the patient are readily separable or openable for cleaning, sterilizing, and inspection purposes without use of tools.

It is an object of the present invention, therefore, to provide such an easily cleanable MIS instrument comprising a handle mechanism including a base handle grippable by a surgeon to hold and manipulate the instrument, a movable handle or trigger for manipulation by the surgeon, and means for providing a movable connection between the base handle and the movable handle. Then, a barrel portion extending away from the base handle is provided, the barrel portion having a distal end portion to be inserted in the patient's body during MIS surgery. A drive actuator extends along the barrel portion to be movable by the movable handle, and means for providing a driving connection between the movable handle and the drive actuator is provided. The driving connection means is preferably disengageable from the drive actuator to permit the drive actuator to be moved away from the barrel portion to permit access for cleaning of the barrel portion and actuator after the MIS surgery.

It is another object of the present invention to provide such a MIS instrument in which the drive actuator is separable from or releasable from the support shaft or barrel portion to accommodate or facilitate the cleaning, sterilizing and inspection activity. In one embodiment of the present invention, the drive actuator is hingedly or pivotally connected to the distal portion of the instrument to be swung away from the handle portion and barrel portion upon release. The distal end of the drive actuator is preferably drivingly connected to the at least one movable member of the operating unit at the distal end of the instrument. When the drive actuator is moved away from the barrel potion, the operating unit and its parts are better exposed for cleaning, sterilizing and inspection.

Still another object of the present invention is to provide a MIS surgical instrument comprising a support shaft having a proximal end extending outside the patient's body during surgery and a distal end extending inside the patient's body during the surgery. The shaft is elongated and generally rigid such that movement of the proximal end relative to the patient will position the distal end within the patient. A handle is rigidly attached to the proximal end of the support shaft to provide means for gripping the instrument. An operating unit is mounted on the distal end of the support shaft for use on and/or viewing tissue within the patient's body. This operating unit has at least one movable action member such as a cutter, grasper or lens for affecting or viewing the patient's tissue within the body. A drive member or drive actuator extends longitudinally along the support shaft to provide a driving connection between the handle and the said at least one action member. This driving connection may be for rectilinear shifting movement or rotating movement. A trigger member is supported on the handle for movement, and means for providing an operative connection between the trigger member and the drive member is provided at the handle such that a surgeon may hold the handle and move the trigger member to move (rotate or shift) the drive member and the at least one action member. In this embodiment, means are provided for releasably connecting the drive member to the instrument such that the drive member can be moved away from the support shaft to accommodate sterilizing, cleaning and inspection of the shaft and the operating unit.

An increasingly recognized major factor in sterilizing instruments is minimizing the amount of both original and remaining bioburden which may contain the pathogens. The design of the present invention minimizes bioburden during surgery and eliminates it after cleaning and sterilizing processes. The design of the present invention is easily serviceable and cleanable without tools for the purpose of preventing serious bacterial and viral infections when the instruments are reused. These features are accomplished in the illustrative and preferred embodiment by having the elongated support shaft or barrel portion formed to have a trough-like slot having a generally U-shaped cross section or at least an open slot extending longitudinally along the support shaft. The drive actuator is illustratively and preferably mounted to move in and out of this slot, to be in the slot during the operation for providing a driving connection between the movable handle or trigger and at least one movable member of the operating unit and to be out of the slot during cleaning, sterilizing and inspection. In the illustrative embodiment, the drive actuator is pivotally or hingedly connected to the distal end of the support shaft or to the movable member of the operating unit and through that member to the support shaft to swing away from the handle portion and the support shaft. In this embodiment, the handle portion is correspondingly slotted to receive the drive actuator. Means are provided within the handle portion to lock the drive actuator in its operating position and means are provided drivingly to connect the movable handle to the drive actuator.

In this illustrative and preferred embodiment, the slotted support shaft and the slotted handle portion receive the drive actuator, and the drive actuator has a cross-sectional shape such that it does not close the support shaft or slot through the handle portion to leave a through passageway communicating from outside the patient to the operating unit at the distal end of the support shaft.

It is another object of the present invention, therefore, to provide such a MIS instrument in which the drive actuator is disposed in a slot in the support shaft and received in a trough or slot in the handle portion to define a passageway through the handle portion and the support shaft through which other instruments such as fiber bundles for laser action or illumination or viewing may be disposed and through which other surgical activities such as laser treatment, viewing or cauterizing may be accomplished. In this embodiment of the present invention, the support shaft, drive actuator and handle are configured to provide a longitudinally directed through passageway for lighting and/or visualization, laser, suction or injection of fluid or gas through the instrument. Fibers or tubes of various types may be placed in or inserted through this passageway. This embodiment contemplates that the traditional cutting or grasping instruments used in MIS surgery may also be used for lighting and/or visualization, laser, suction or injection of liquid or gas, as well as other types of treatment processes such as cauterizing.

It is still another object of the present invention to provide a finger-operable lock which secures the drive actuator in its operating position relative to the support shaft and instrument handle. This finger-operable lock releases the actuator to pivot or swing at the distal end of the support shaft fully out of the slot in the support shaft to accommodate cleaning.

Further to enhance the cleanability of the MIS instrument of the present invention, the support shaft itself is connected to the handle portion for easy separation simply by releasing a finger-actuated locking mechanism. In the illustrative and preferred embodiment, the proximal end of the support shaft is proportioned and designed to slide into a receiver section, preferably an open slotted portion of the handle, to be snugly received in the receiver section and firmly attached to the handle by the finger-actuated locking mechanism. Another feature of the illustrative and preferred embodiment is to have the operating unit, for instance the scissors or graspers, at the distal end of the support shaft also be removably attached to the distal end for cleaning and/or replacement.

It is still a further object of the present invention, therefore, to have a MIS instrument of the type discussed above in which the drive actuator is removable or releasable from the support shaft and handle also to have the support shaft be removable or releasable from the handle and to have the operating unit removable or releasable from the distal end of the support shaft.

In another embodiment of the present invention the support member of the surgical instrument is curved to facilitate accessibility by a surgeon. In this instance, the drive actuator is configured to include the plurality of notched or relieved sections at a location adjacent the curved portion of the support member. The curved support member has an operating unit formed integrally with a distal end. A proximal end of the curved support member is configured to be removably coupled to an open end of the handle assembly.

The body of the handle assembly is advantageously configured to allow easy removal of the tip assembly from the handle body by a surgeon in the field. The primary purpose for such removability is to permit field repairability by like kind tip assemblies. In other words, a surgeon can remove a tip assembly for repair or replacement with a like kind tip assembly without having to send the entire surgical instrument back to the manufacturer for repair. Thus by having a spare tip assembly on hand, the instrument can be returned to service before the next surgery.

The design of the body of the handle assembly also advantageously permits quick removal of the tip assembly from the handle body by a surgeon in the operating room. Therefore, a surgical kit may be provided for use by a surgeon during an operation. The kit includes a handle assembly and a plurality of different tip assemblies which each include the elongated support member having a proximal end configured to be removably coupled to the handle assembly and an operating unit formed at a distal end of the support member for performing a particular surgical procedure. The plurality of tip assemblies in the kit include straight support members and both right curved support members and left curved support members. In addition, various types of instruments may be included for the operating units on the straight and curved support units. For example, cutters, graspers, forceps, punches, scissors, or any other type of surgical instrument can be formed on the distal end of the straight and curved tip assemblies in the kit. Advantageously, a surgeon can quickly unlock and remove a particular tip assembly from the handle during a surgical procedure. For instance, the surgeon could remove a straight tip assembly and decide to insert a right curved or left curved tip assembly to facilitate a particular surgical procedure. The kit of the present invention makes it possible for the surgeon to quickly remove and select a most advantageous tip assembly for use in the surgical procedure. Therefore, the kit of the present invention advantageously provides the surgeon the ability to replace the entire tip assembly in seconds, even in the sterile field during surgery. In addition, because the tip assemblies are removable from the handle, the entire instrument does not have to be returned to the manufacturer for repair. This has many advantages, particularly eliminating the transportation of possibly hazardous bioburden, and not having the instrument out of service for up to the several weeks. This greatly reduces costs.

Another advantage of the present invention is that the various components of the tip assembly are coupled together to prevent the components of the tip assembly from being separated or disassembled. If the tip assembly were disassembled, it is likely that it would take an extended period of time to reassemble the small parts without a microscope or magnifier. Such disassembly would also increase the likelihood of damage to the components of the tip assembly. The drive actuator is locked into the operating unit by a round cylinder on one side of the distal end of the actuator which is inserted into the recess of the operating unit. A side plate or stop is welded on to the operating unit, preventing disassembly of the operating unit from the drive actuator. Finally, after assembly of the cutter/actuator sub-assembly into the tip, a pair of stops are welded to the tip to prevent the operating unit from rotating out of or derailing from the tip pivot arc on the support member. Therefore, the tip assembly cannot be disassembled either accidentally or on purpose without major force and destruction of the tip assembly.

According to one aspect of the present invention, a surgical instrument includes a handle having a movable trigger, and an elongated support member having a proximal end coupled to the handle and a distal end for insertion into a patient's body. The elongated support member includes a curved portion located in close proximity to the distal end. The elongated support member is formed to include a slot extending from the proximal end to the distal end. The surgical instrument also includes an operating unit coupled to the distal end of the support member, and a drive actuator configured to be positioned in the slot of the support member. The drive actuator has a distal end and a proximal end. The distal end of the drive actuator is coupled to the operating unit and the proximal end of the drive actuator is configured to engage the trigger so that the drive actuator moves the operating unit relative to the support member in response to movement of the trigger.

In the illustrated embodiment, the drive actuator has a predetermined thickness and includes a relieved section having a reduced thickness located adjacent the curved portion of the support member. This relieved section of the drive actuator permits the drive actuator to bend as it moves through the curved portion of the support member. The relieved section includes a plurality of spaced apart ribs having substantially the predetermined thickness to position the relieved section of the drive actuator in the slot of the support member.

Also in the illustrated embodiment, the surgical instrument includes a locking member for removably coupling the proximal end of the drive actuator to the handle. The locking member is movable from a first position to hold the drive actuator in a locked position relative to the handle to a second position to release the drive actuator from the handle and to permit movement of the drive actuator away from the handle. Such pivotal movement of the device actuator permits cleaning, sterilization, and inspection of the support member, the drive actuator, and the operating unit after a surgical procedure.

According to another aspect of the present invention, a surgical instrument includes a handle having a movable trigger, an elongated support member having a proximal end coupled to the handle and a distal end for insertion into a patient's body, an operating unit pivotably coupled to the distal end of the support member, and a drive actuator having a distal end and a proximal end. The proximal end of the drive actuator is configured to engage a portion of the movable trigger, and the distal end of the drive actuator is pivotably coupled to the operating unit for moving the operating unit relative to the support member in response to movement of the trigger. The surgical instrument also includes a first stop formed on the operating unit to prevent disengagement of the distal end of the drive actuator from the operating unit, and a second stop formed on the support member to prevent disengagement of the operating unit from the support member.

According to yet another aspect of the present invention, a surgical instrument includes a removable tip assembly having an elongated support member including a proximal end configured to be coupled to the handle and a distal end for insertion into a patient's body. The tip assembly also includes an operating unit coupled to the distal end of the support member, and a drive actuator having a distal end and a proximal end. The distal end of the drive actuator is pivotably coupled to the operating unit for moving the operating unit relative to the support member. The surgical instrument also includes a handle having a body portion formed to include an opening for slidably receiving the proximal end of the tip assembly therein, a movable trigger configured to actuate the operating unit of the selected tip assembly, and a locking mechanism for removably coupling the selected tip assembly to the handle. Using only a simple screwdriver type tool, the locking mechanism is movable from a first position to hold the selected tip assembly in a locked position relative to the handle to a second position to release the selected tip assembly from the handle and permit the removal of the selected tip assembly from the handle.

In the illustrated embodiment, the locking mechanism includes a semi-cylindrical member for engaging a notch formed in the support member to secure the support member to the handle. The locking mechanism also includes means coupled to the semi-cylindrical member for rotating the semi-cylindrical member to release the support member from the handle.

According to still another aspect of the present invention, a surgical instrument kit is provided. The kit includes a first removable tip assembly including a straight support member having a proximal end configured to be coupled to the handle and a distal end for insertion into a patient's body. The distal end of the support member of the first tip assembly is formed to include an operating unit thereon. The kit also includes a second removable tip assembly including a curved support member having a proximal end configured to be coupled to the handle and a distal end for insertion into the patient's body. The distal end of the curved support member is formed to include an operating unit thereon. The kit further includes a handle having a body portion configured to receive the proximal end of a selected one of the first and second tip assemblies therein, a movable trigger configured to actuate the operating unit of the selected tip assembly, and a locking mechanism for removably coupling the selected tip assembly to the handle. The locking mechanism is movable from a first position to hold the selected tip assembly in a locked position relative to the handle to a second position to release the selected tip assembly from the handle and permit the removal of the selected tip assembly from the handle.

Additional objects, features, and advantages of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which:

FIG. 1 is an elevational view of a surgical instrument of the present invention including a handle assembly, a support member, an operating unit, and a movable drive member for controlling movement of the operating unit relative to the support member;

FIG. 2 is a perspective view illustrating one embodiment of an operating unit which is illustratively a cutter and illustrating a distal end of the drive member configured to be coupled to the cutter;

FIG. 3 is a sectional view of the distal end of the surgical instrument illustrating the configuration of an illustrated embodiment of the operating unit, the support member, and the drive member when the drive member is in its extended position to deflect the operating unit toward the support member;

FIG. 4 is a sectional view similar to FIG. 3 in which the drive member is in its retracted position to move the operating unit away from the support member;

FIG. 11 is a top plan view of a curved tip assembly of the present invention including a curved support member having a proximal end configured to be removably coupled to the handle assembly and a distal end having an operating unit coupled thereto, and a drive actuator having a relieved section for moving through a curved slot formed in the support member to actuate the operating unit;

FIG. 12 is a side elevational view illustrating the tip assembly of FIG. 11 attached to the handle assembly;

FIG. 13 is a partial perspective view further illustrating the drive actuator including the relieved portion and a plurality of ribs for moving through the curved section of the curved tip assembly of FIGS. 11 and 12;

FIG. 14 is a sectional view taken through the distal end of the tip assembly illustrating an operating unit and welded stops to prevent disassembly of the tip assembly;

FIG. 15 is a bottom plan view of the tip assembly of FIG. 14;

DETAIL DESCRIPTION OF THE DRAWINGS

Figure 5:
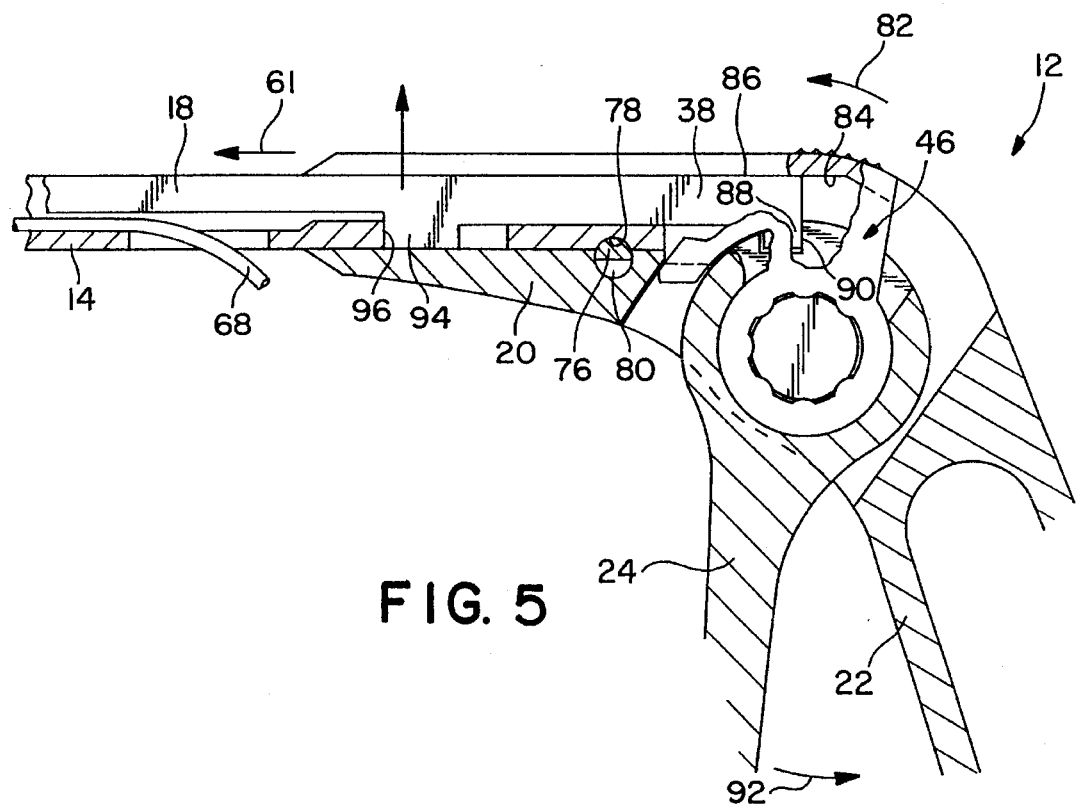
FIG. 5 is a sectional view taken through the handle assembly of the present invention which the handle is positioned to move the drive member to its extended position and illustrating a first locking member for releasably coupling the support member to the handle and a second locking member for releasably coupling the drive member to the handle.

Referring now to the drawings, FIG. 1 illustrates a reusable MIS surgical instrument 10 of the present invention. Surgical instrument 10 includes a handle assembly 12, a support member 14, an operating unit 16, and an actuator or drive member 18. Handle assembly 12 includes a body portion 20, a base handle portion 22 formed integrally with body portion 20, and a movable handle portion 24 pivotably coupled to body portion 20 in a conventional manner by coupler assembly 26. Support member 14 is elongated and includes a proximal end 28 releasably coupled to handle body 20 by lock mechanism 30. Support member 14 also includes a distal end 32 for insertion into a patient's body during an operation and a longitudinal axis 34 extending from proximal end 28 to distal end 32.

Operating unit 16 is pivotably coupled to distal end 32 of support member 14. Operating unit 16 can be separated from support member 14 and removed. In the illustrated embodiment, operating unit 16 will be described with reference to a cutter 36. However, it is understood that other operating units 16 other than cutter 36 may be used in connection with the present invention. Therefore, operating unit 16 of the present invention is not limited to cutter 36. For instance, operating unit 16 may be used to guide either a permanent or single use illumination or optical line, fiber optic bundle or tube for providing illumination, vision, laser, etc. at distal end 32 of support member 14 for use during a surgical procedure. In addition, liquid or gas suction or injection tubes may be coupled to operating unit 16 for control by drive member 18 during the surgical procedure. Various other types of instruments could be included for operating unit 16 including cutters, graspers, forceps, punches, scissors, or any other surgical instrument.

Drive member 18 includes a proximal end 38 configured to be releasably coupled to body portion 20 of handle assembly 12. Drive member 18 also includes a distal end 40 coupled to cutter 36 to control movement of cutter 36 relative to support member 14 when drive member 18 moves relative to support member 14. Drive member 18 also includes a longitudinal axis 42 extending from proximal end 38 to distal end 40. As illustrated in FIG. 1, drive member 18 is movable or pivotable away from handle 20 so that longitudinal axis 34 of support member 14 is aligned at an angle relative to longitudinal axis 40 of drive member 18 as illustrated by angle 44. During a surgical procedure, drive member 18 is pivoted so that longitudinal axis 42 of drive member 18 is aligned generally parallel to longitudinal axis 34 of support member 14. Drive member 18 is coupled to handle body 20 by locking mechanism 46 as discussed in detail below.

Movable handle portion 24 then moves back and forth in the direction of double-headed arrow 48 to move drive member 18 relative to support member 14 and thereby control movement of operating unit 16 relative to support member 14. After the surgical procedure is complete, locking mechanism 46 is moved to release drive member 18 from handle body 20 so that drive member 18 may pivot to its open position illustrated in FIG. 1. This facilitates cleaning, sterilization, and inspection of the drive member 18, operating unit 16, support member 14, and handle assembly 12. The inspection will permit the surgeon or operator to inspect the surgical instrument 10 more carefully and increase the likelihood of detecting any bioburden which may remain on the instrument 10 after the cleaning and sterilization procedure, thereby permitting removal of the detected bioburden.

FIG. 2 illustrates the cutter 36 of the present invention. The cutter 36 includes a head 50 and a body 52 formed to include a notch therein. Distal end 40 of drive member 18 is formed to include a truncated cylindrical projection 55 extending therefrom. Top and bottom portions of cylindrical projection 55 are cut flat and are spaced apart by a distance illustrated by dimension 56. Dimension 56 is less than dimension 57 of notch 54 so that cylindrical projection may be inserted into notch 54 when drive member is aligned at a 90° angle relative to body 52. Once inside notch 54, cylindrical projection 55 can rotate relative to cutter 36 and will not dislodge from notch 54 at an angle of less than 90°.

Cutter 36 is pivotably coupled to support member 14 by arcuate grooves 59 formed on opposite sides of cutter 36 which are engaged by arcuate tracks 60 formed on support member 14. Therefore, cutter 36 is pivotably coupled to support member 14. Arcuate tracks 60 have a center illustrated at location 65 which is near a bottom surface of support member 14. The combination of the arcuate coupling arrangement and the truncated conical pivotable coupling arrangement for moving operating unit 16 provides advantages over and is cheaper to build than known coupling arrangements such as the arrangement illustrated in U.S. Pat. No. 4,712,545.

FIG. 3 illustrates drive member 18 in an extended position moved in the direction of arrow 61 toward distal end 32 of support member 14 to move cutter 36 in the direction of arrow 62 toward support member 14. Illustratively, support member 14 includes a head portion aligned at an angle relative to longitudinal axis 34 of support member 14 to facilitate cutting of tissue by cutter 36. Head 64 includes an open portion 66 for receiving cutter head 50 therein. An illumination line, optical line, fiber optic bundle, tube, or other means 68 may be located in a trough-like slot 70 formed in support member 14. Line 68 may provide illumination, optical viewing, irrigation, suction, electrocauterization, or other function to distal end 32 of support member 14. As discussed above, line 68 may be coupled to operating unit 16 so that the end of line 68 is movable relative to distal end 32 of support member 14. Therefore, a surgeon can direct the end of line 68 to a desired position. In other words, operating unit 16 may have the sole function of maneuvering illumination and/or viewing optics.

Because drive member 18 can move to an open position relative to support member, instrument 10 facilitates insertion of a single use illumination or viewing line, fiber optic bundle, etc. into the passageway or channel defined between slot 70 of support member 14 and drive member 18. Installation of such a single use device is much easier than threading the device through a conventional tube enclosed instrument.

FIG. 4 illustrates drive member 18 in its retracted position. As drive member 18 moves to its retracted position in the direction of arrow 72, cutter 36 moves away from support member 14 in the direction of arrow 74. Therefore, movement of the drive member 18 back and forth in the directions of arrows 61 in FIG. 3 and 72 in FIG. 4 cause pivotable movement of cutter 36 relative to support member 14.

Figure 6:
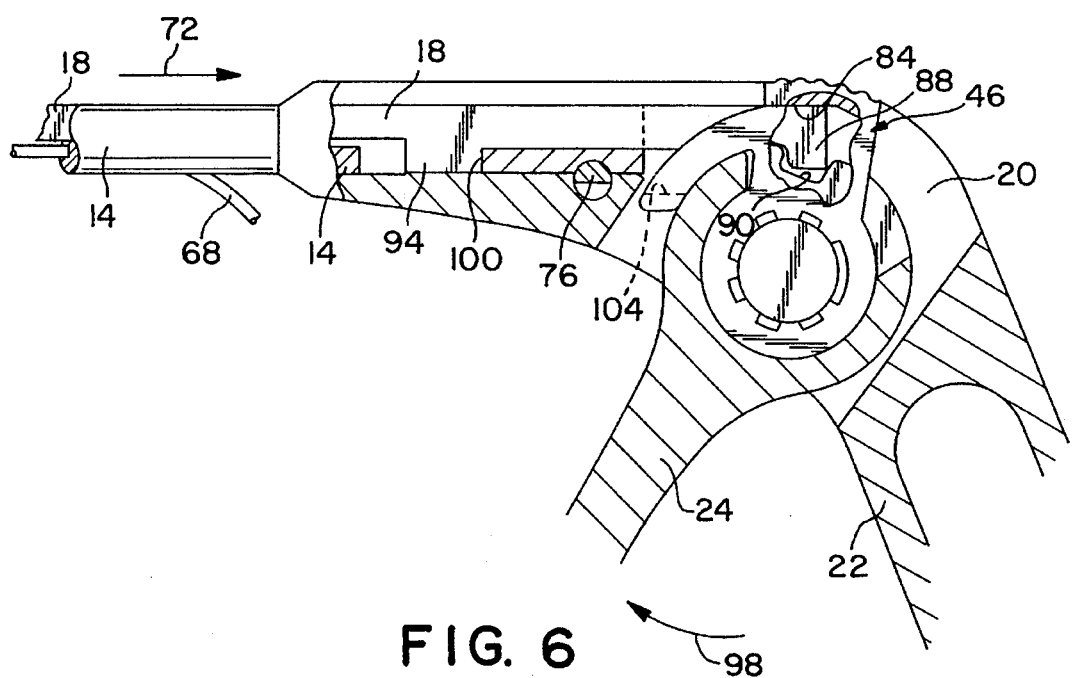
FIG. 6 is a sectional view similar to FIG. 5 in which a movable portion of the handle has been pivoted away from a base portion of the handle to move the drive member to its retracted position.
Figure 7:
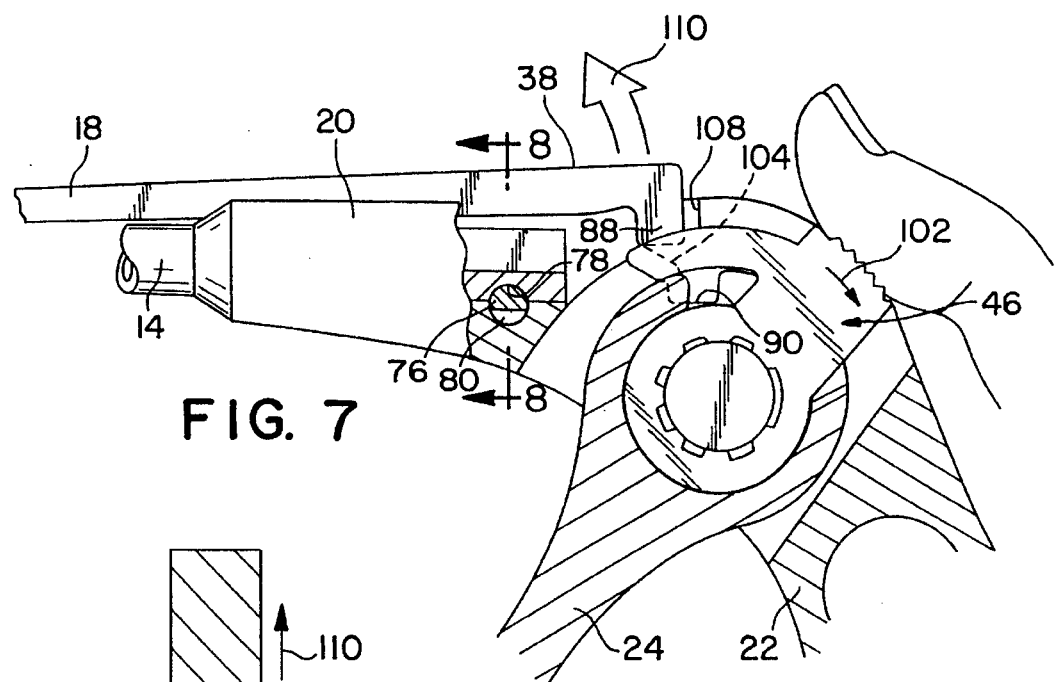
FIG. 7 is a sectional view similar to FIGS. 5 and 6 in which the second locking member is moved relative to the handle to release the drive member from the handle so that the drive member pivots away from the handle and the support shaft to permit cleaning, sterilization, and inspection of the drive member, the support member, and the operating unit.

FIGS. 5–7 illustrate the configuration of the handle assembly 12 for releasably coupling support member 14 and drive member 18 to handle assembly 12. Support member 14 is coupled to handle body 20 by a semi-cylindrical lock rod 76 which engages a notch 78 formed in support member 14. When lock rod 76 is rotated so that open portion 80 is directed toward support member 14, support member 14 can be removed from handle body 20 as discussed below.

Lock member 46 for coupling drive member 18 to handle body 20 is spring-biased in the direction of arrow 82 in FIG. 5 so that a locking surface 84 engages top surface 86 of drive member 18 to hold distal end 38 of drive member 18 within handle body 20. A tab 88 of drive member is inserted into notch 90 of movable handle portion 24 to couple drive member 18 to movable handle portion 24. In the FIG. 5 embodiment, movable handle 24 has been closed in the direction of arrow 92 to move drive member 18 to its extended position in the direction of arrow 61. In the extended position of FIG. 5, a second tab 94 on drive member 18 engages a first blocking surface 96 of support member 14 to block further movement of drive member 18 in the direction of arrow 61.

FIG. 6 illustrates the configuration of movable handle 24 and drive member 18 when drive member 18 is in its retracted position. Notch 90 of movable handle portion 24 forces drive member 18 in the direction of arrow 72 upon movement of movable handle portion 20 in the direction of arrow 98. Tab 94 of drive member 18 engages a second blocking surface 100 of support member 14 to block further movement of drive member 18 in the direction of arrow 72.

After a surgical procedure is performed and it is desired to open drive member 18 relative to support tube 14, a user moves locking member 46 in the direction of arrow 102 in FIG. 7 so that a lifting release surface 104 of locking member 46 engages bottom surface 106 of tab 88 of drive member 18 to lift proximal end 38 of drive member 18 upwardly out of a slot 108 formed in handle body 20 in the direction of arrow 110. Therefore, drive member 18 can be moved to its open position illustrated in FIG. 1, in which longitudinal axis 42 of drive member 18 is aligned at an angle relative to longitudinal axis 34 of support member 14 to facilitate cleaning and sterilization of surgical instrument 10 and advantageously to permit inspection of drive member 18, support member 14, operating unit 16, and handle assembly 12 to detect any remaining contamination after the cleaning and sterilization procedure.

Figure 8:
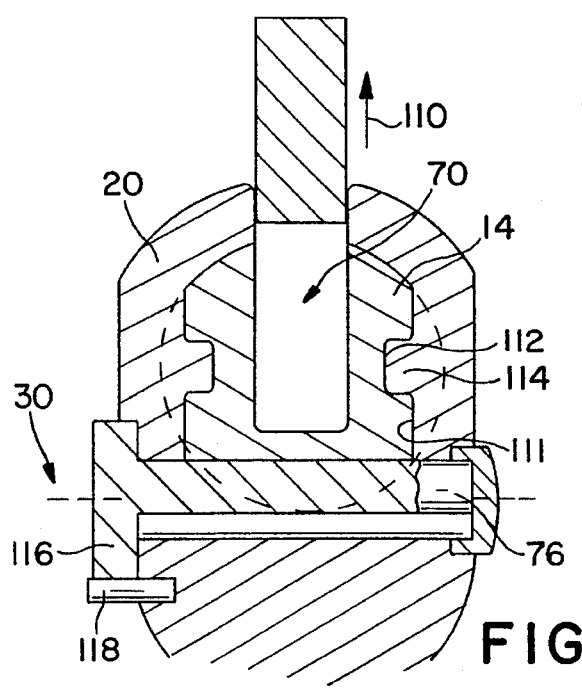
FIG. 8 is a sectional view taken along lines 8—8 of FIG. 7 illustrating the configuration of the support member within the handle, the drive member within a slot formed in the handle and the support member, and the configuration of the first locking member for locking the support member to the handle.
Figure 9:
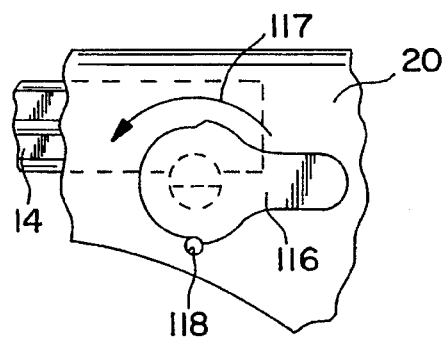
FIG. 9 is a partial elevational view with portions broken away illustrating operation of the first locking member.
Figure 10:
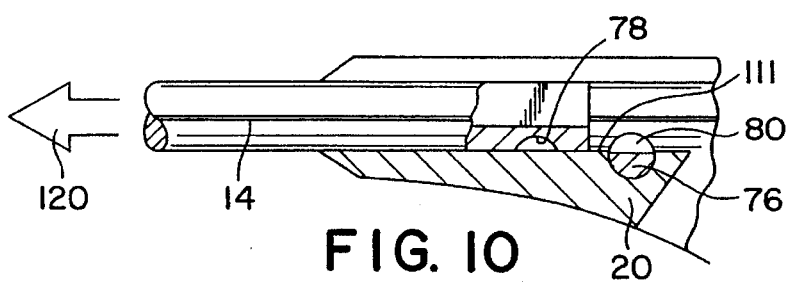
FIG. 10 is a sectional view with portions broken away illustrating removal of the support member from the handle assembly after the first locking member has been pivoted to its release position.

FIG. 8 illustrates the configuration of the cross section of proximal end 28 of support member 14 located within body portion 20 of handle assembly 12. Support member 14 is formed to include notched sections 112 for receiving tabs 114 of body portion 20 therein to align support member 14 relative to body portion 20 and to prevent rotation of support member 14 relative to handle body 20. FIGS. 8 and 9 also illustrate a lever 116 coupled to semi-cylindrical lock rod 76. As illustrated in FIG. 9, lever 116 is rotatable in the direction of arrow 117 to release support member 14 from handle body 20. A limit pin 118 is rigidly coupled to handle body portion 20 to limit movement of lever 116. When lever 116 is rotated in the direction of arrow 117 by 180°, open section 80 of cylindrical locking member 76 is aligned in a direction facing support member 14 as illustrated in FIG. 10. In this "release" position, the support member 14 can be removed from handle body portion 20 in the direction of arrow 120. Therefore, support member 14 can be cleaned or replaced.

When it is desired to insert a new support member into handle body 20, lever 116 is rotated to align the semi-cylindrical lock in the position illustrated in FIG. 10, and support member 14 is inserted into opening 111 formed in body portion 20. Once arcuate notch 78 is aligned with lock member 76, lever 116 is rotated to the position illustrated in FIG. 9 to lock support member 14 in position relative to handle body 20. A surgeon then moves locking member 46 in the direction of arrow 102 in FIG. 7 to permit drive member 18 to pass through slot 108 formed in handle body portion 20 and into trough-like slot 70 formed in support member 14. The surgeon then releases locking member 46 so that locking member 46 is moved by the spring in the direction of arrow 82 in FIG. 5 to the position illustrated in FIGS. 5 and 6 to lock distal end 38 of drive member 18 to handle body 20. The surgeon can then control movement of drive member 18 and operating unit 16 by moving movable handle portion 24 back and forth in the direction of double-headed arrows 48. It is understood that conventional drive assemblies may be used to rotate drive member 18 relative to support member 14 about its longitudinal axis 42 instead of providing linear movement of drive member 18 relative to support member 14. In this rotary embodiment, the rotating drive member can be used to drive a rotating cutting instrument or other operating unit 16 at the distal end 32 of support member 14.

Another embodiment of the present invention is illustrated in FIGS. 11–16. In this embodiment, the tip assembly 140 is advantageously curved to facilitate accessibility by a surgeon during a surgical procedure. FIG. 11 illustrates a curved tip assembly 140 for use with the handle assembly 12. Curved tip assembly 140 includes a curved support member 142 having a proximal end 144 configured to be coupled to handle assembly 12 and a distal end 146 formed to include an operating unit 148. Illustratively, operating unit 148 includes a head portion 150 and a movable cutter 152 pivotably coupled to head portion 150. A drive actuator 154 is located within an elongated slot 156 formed in support member 142. In order for drive actuator 154 to move back and forth in the directions of double headed arrow 158 in FIG. 11, drive actuator 154 is formed to include a relieved section 160 to permit drive actuator 154 to bend as it moves through curved section 162 of support member 142.

As illustrated in FIG. 12, tip assembly 140 is configured to be removably coupled to the same handle assembly 12 as the straight support member 14 illustrated in FIGS. 1–10. In a FIG. 12 embodiment, lock mechanism 30 illustrated in FIG. 1 has been replaced by lock mechanism 164 on an opposite side of handle assembly 12. Lock mechanism 164 is configured to include a slotted head 166 for actuation by a tool to rotate locking mechanism and move the semi-cylindrical lock rod 76 to lock and unlock tip assembly 140. When it is desired to remove tip assembly 140, lock mechanism 164 is moved to a release position to align and open portion 80 of lock rod 76 toward support member 142 to permit support member 142 to be easily removed from handle body 20. The primary purpose for such removability is to permit field repairability by like kind tip assemblies. In other words, a surgeon can remove a tip assembly 140 for repair or replacement with a like kind tip assembly without having to send the entire surgical instrument back to the manufacturer for repair.

Also advantageously, tip assembly 140 can be replaced with another desired tip assembly. For instance, the tip assembly 140 can be replaced with a straight tip assembly such as illustrated in FIG. 1. In addition, tip assembly can be selected from a kit including left curved, straight, and right curved tip assemblies. In addition, a surgeon may desire to use another operating unit during the surgical procedure. Therefore, tip assembly 140 can be replaced with a left curved, straight, or right curved tip assembly having any other type of operating unit at its distal end. The ability to easily remove and replace tip assembly 140 provides a significant advantage of the present invention and provides great flexibility to the surgeon to repair or replace the tip assembly, even during the surgical procedure.

Referring again to FIG. 12, as the movable handle 24 is moved relative to handle body 20 from the solid line position to the dotted line position, cutter 152 moves to the dotted position of FIG. 12. In other words, movement of movable handle portion 24 moves drive actuator 154 back and forth in the direction of double headed arrows 158 inside slot 156 of support member 142 to control movement of operating unit 148.

It is understood that other types of drive actuators may be used in accordance with the present invention. For instance, the drive actuator may be made in two separate articulated sections capable of pivoting relative to each other. A first smaller section located near the distal end is a curved section. A longer straight section extends from the curved section toward the proximal end of the tip assembly. The two sections are pivotably coupled together. In this embodiment, both drive actuator sections are openable for cleaning, and inspection. The drive actuator may also be rotatable in the support member 142. In this embodiment, a gear mechanism is provided on the proximal end of the drive actuator. The gear on the drive actuator cooperates with a complementary gear in the handle assembly for rotating the drive actuator about its longitudinal axis within the support member. Again, this rotating drive actuator is openable for cleaning and inspection.

FIG. 13 further illustrates the drive actuator 154 for use with a curved support member 142. Relieved section 160 includes a plurality of relieved or notched sections 168 having a reduced thickness as compared to the thickness of main body portion 170 of drive actuator 154. Relieved section 160 includes a plurality of ribs 172 having a thickness substantially equal to the thickness of the main body portion 170. Ribs 172 maintain the position of drive actuator inside slot 156 during movement of drive actuator 154. Ribs 172 may be located closer together than illustrated in FIG. 13. It is understood that other designs, without ribs 172 may be used in accordance with this invention. Distal end 174 of drive actuator 154 is formed to include a truncated cylindrical projection 176 similar to projection 55 illustrated in FIG. 2. Projection 176 is configured to enter a notch 177 formed in cutter 152 to provide movement of cutter 152 relative to support member 142.

FIGS. 14 and 15 illustrate the improved operating unit design of the embodiments of FIGS. 11–16. Cutter 152 is slidably coupled to cylindrical projection 176 and to arcuate tracks 180 formed on support member 142. However, in FIGS. 14 and 15, a pair of stops 182 are formed on bottom surface 184 of support member 142 to prevent or block movement of cutter 150 beyond stops 182 in the direction of arrow 186 in FIG. 14. This prevents removal or disengagement of cutter 152 from support member 142. Stops 182 are formed on bottom surface 184, for example, by welding. It is understood that a pin extending through cutter 152 and support member 142 may be used to pivotably couple cutter 152 to support member 142. In this case, stops 182 would not be required.

Projection 176 is installed into a complementary opening 177 formed in the cutter in a direction from the side of cutter 152. A stop or side plate 188 is then welded to cutter 152 to secure drive actuator 154 to cutter 152. Side plate 188 prevents cylindrical projection 176 from being disengaged from opening 177 formed in cutter 152. Therefore, stops 182 and side plate 188 advantageously couple support member 142, cutter 152, and drive actuator 154 together as a single unit. Drive actuator 154 can be pivoted upwardly in as illustrated by arrow 110 in FIG. 17 to facilitate cleaning of tip assembly 140. However, drive actuator 154, support member 142, and cutter 152 are prevented from being accidentally or purposely disassembled. This eliminates the time which would be required to reassemble the small parts upon disassembly. Requiring such reassembly could damage the parts.

Figure 16:
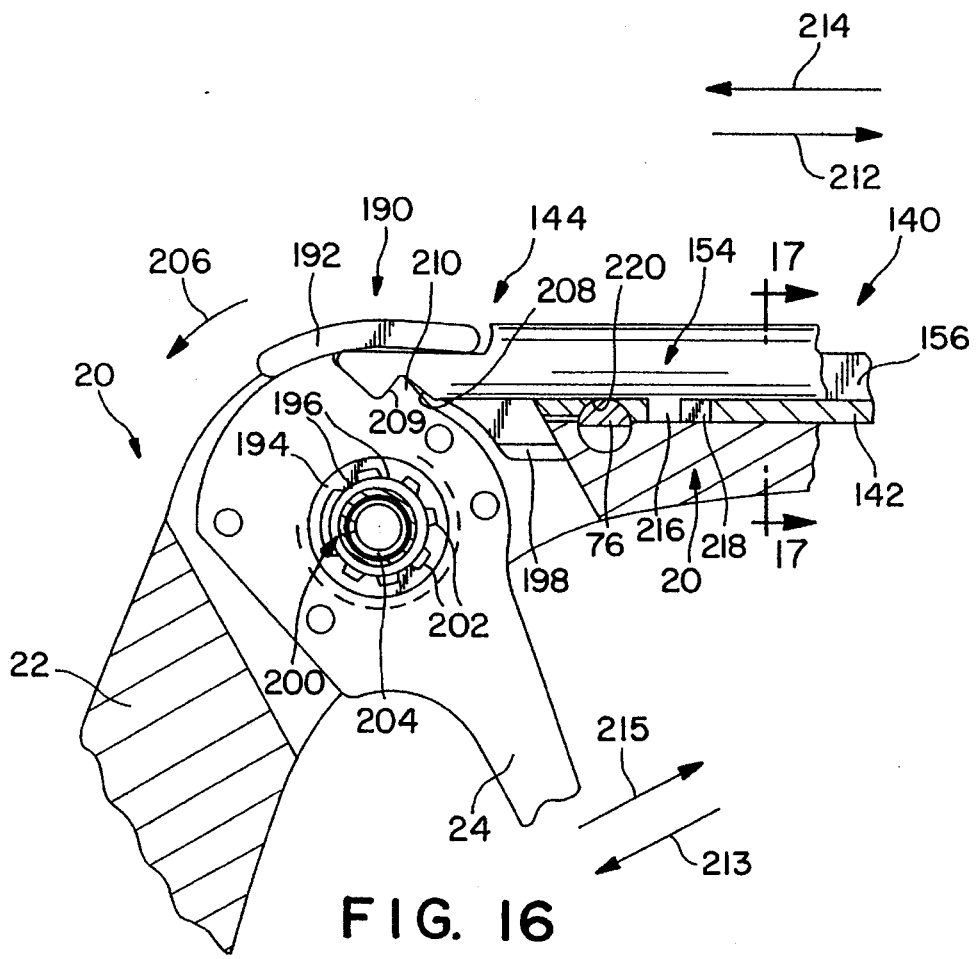
FIG. 16 is a partial sectional view taken through the handle assembly of FIG. 12 illustrating the configuration of the proximal end of the tip assembly engaging the handle assembly to provide movement of the drive actuator of the tip assembly to actuate the operating unit.

A further embodiment of the proximal end of the tip assembly is illustrated in FIG. 16. In the FIG. 16 embodiment, handle assembly 20 includes a rotatable locking mechanism 190 including a lock surface 192, a central hub 194 having a plurality of teeth 196 formed thereon, and a lifting release surface 198. Lock mechanism 190 is held in position by a splined button 200 formed to include a plurality of teeth 202 which engage teeth 196 on cylindrical hub 194 to hold locking mechanism 190 in the locked position illustrated in FIG. 16. Splined button 102 is held in engagement with locking mechanism 190 by a spring 204. When it is desired to unlock locking mechanism 190 to permit removal of tip assembly 140 or to permit movement of the proximal end of drive actuator 154 to its upwardly pivoted position to permit cleaning or inspection, the splined button 200 is depressed against the force of spring 204 to disengage teeth 202 of button 200 from teeth 196 of cylinder hub 194. This permits rotation of locking mechanism 190 in the direction of arrow 206. Such rotation moves locking surface 192 from its locked position above distal end 144 of tip assembly 140 to an open position. Lifting surface 198 moves the proximal end of drive actuator 154 out of slot 156 of support member 142.

The drive actuator 154 includes a notched portion defined by walls 208 and 209 which engages a drive portion 210 on movable handle 224. Preferably, drive portion 210 has a triangular shape to engage first surface 208 of drive actuator 154 to move drive actuator 154 in the direction of arrow 212 when movable handle portion 24 moves in the direction of arrow 213. Drive portion 210 engages second drive surface 209 to move drive actuator 154 in the direction of arrow 214 when movable handle portion 24 moves in the direction of arrow 215.

Drive actuator 154 includes a tab 216 which moves back and forth inside slot 218 formed in support member 142. Therefore, slot 218 limits the range of movement of drive actuator 154 relative to support member 142. Support member 142 further includes a notched section 220 configured to be engaged by lock rod 76 to lock tip assembly 140 in position relative to handle assembly 20.

The drive assembly illustrated in FIG. 16 reduces bowing of actuator 154 out of the elongated slot 156 of support member 142 as drive actuator 154 moves back and forth in the direction of arrows 212 and 214.

Figure 17:
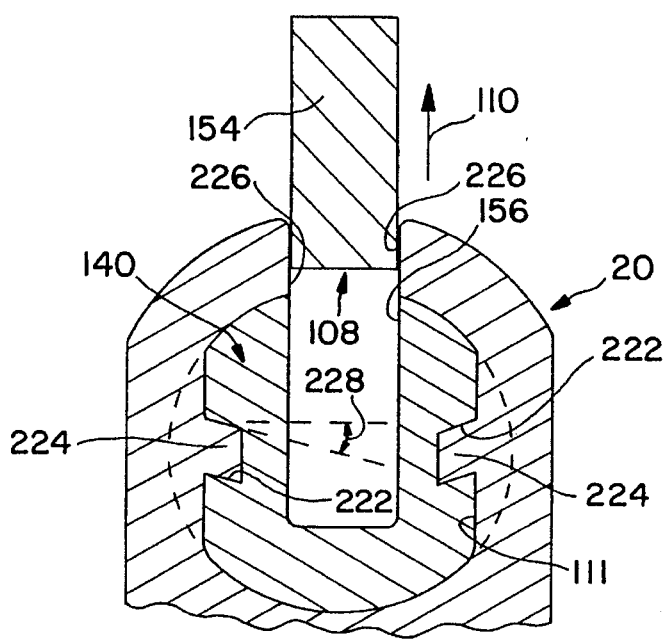
FIG. 17 iS a sectional view taken along lines 17—17 of FIG. 16 illustrating the configuration of the support member within the handle.

Another feature of the present invention is illustrated in FIG. 17. FIG. 17 illustrates the configuration of the cross section of proximal end 144 of support member 142 located within body portion 20 of handle assembly 12. Proximal end 144 of support member 142 is slidably inserted into opening 111 formed in body portion 20 of handle 12. Support member 142 is formed to include angled notched sections 222 for receiving tabs or tracks 224 formed on body portion 20 of handle 12 therein to align support member 142 relative to body portion 20 and to prevent rotation of support member 142 relative to handle body 20. Tracks 22 are not perpendicular to side walls 226 which define slot 108 in handle body 20 like tabs 114 of FIG. 8. Instead, tracks 224 are aligned downwardly at a predetermined angle relative to side walls 226 as illustrated by angle 228. Angle 228 is preferably between about 6° and about 10°. This spline configuration of tracks 224 on handle body 20 and the mating angled slots 222 of proximal end 144 of support member 142 advantageously neutralizes lateral forces occurring on tip assembly 140 during a surgical procedure to prevent spreading of the slot 108 in handle body 20 when a prying force is applied to the tip assembly 140 during the surgical procedure. Therefore, a tight fit is maintained between the proximal end 144 of support member 142 and the opening 111 formed in handle body 20. It is understood that the positions of tracks 224 and slots 222 may be reversed. In other words, tracks 224 may be formed on support member 142 and slots 222 may be formed in handle body 20.

Although the invention has been described in detail with reference to a certain preferred embodiment, variations and modifications exist within the scope and spirit of the invention as described and defined in the following claims.

What is claimed is:

1. A surgical instrument comprising:

a handle including a movable trigger;

an elongated support member having a proximal end coupled to the handle and a distal end for insertion into a patient's body, the elongated support member including a curved portion located in close proximity to the distal end, the elongated support member being formed to include an opened trough slot extending from the proximal end to the distal end;

an operating unit coupled to the distal end of the support member; and a drive actuator configured to be positioned in the slot of the support member, the drive actuator having a distal end and a proximal end, the distal end of the drive actuator being coupled to the operating unit and the proximal end of the drive actuator being configured to engage the trigger so that the drive actuator moves the operating unit relative to the support member in response to movement of the trigger.

2. The surgical instrument of claim 1, further comprising a locking member for removably coupling the proximal end of the drive actuator to the handle, the locking member being movable from a first position to hold the drive actuator in a locked position relative to the handle to a second position to release the drive actuator from the handle and to permit movement of the drive actuator away from the handle to permit cleaning, sterilization, and inspection of the support member, the drive actuator, and the operating unit after a surgical procedure.

3. The surgical instrument of claim 2, wherein the drive actuator is inserted into a slot formed in the handle to couple the drive actuator to the handle, and wherein the locking member includes an ejector for ejecting the drive actuator from the slot upon movement of the locking member to its second position.

4. The surgical instrument of claim 1, wherein a proximal end of the support member is inserted into a slot formed in the handle to couple the support member to the handle, and further comprising a locking mechanism for removably coupling the support member to the handle.

5. The surgical instrument of claim 1, further comprising a single use illumination, optical, or laser line located in the elongated slot of the support member.

6. The surgical instrument of claim 1, wherein the drive actuator includes a projection extending outwardly therefrom and the operating unit is formed to include an opening therein for receiving the projection therein to pivotably couple the drive actuator to the operating unit.

7. The surgical instrument of claim 6, further comprising a side plate coupled to the operating unit to prevent the projection from disengaging the opening of the operating unit.

8. The surgical instrument of claim 1, wherein the operating unit is pivotably coupled to the support member and further comprising at least one stop formed on the support member to prevent disengagement of the operating unit from the support member.

9. The surgical instrument of claim 8, wherein the drive actuator is pivotably coupled to the operating unit and further comprising at least one stop formed on the operating unit to prevent disengagement of the drive actuator from the operating unit.

10. The surgical instrument of claim 8, wherein the operating unit is coupled to the support member by an arcuate groove and notch arrangement to couple the operating unit to the support member.

11. A surgical instrument comprising:

a handle including a movable trigger;

an elongated support member having a proximal end coupled to the handle and a distal end for insertion into a patient's body, the elongated support member including a curved portion located in close proximity to the distal end, the elongated support member being formed to include a slot extending from the proximal end to the distal end;

an operating unit coupled to the distal end of the support member;

a drive actuator configured to be positioned in the slot of the support member, the drive actuator having a distal end and a proximal end, the distal end of the drive actuator being coupled to the operating unit and the proximal end of the drive actuator being configured to engage the trigger so that the drive actuator moves the operating unit relative to the support member in response to movement of the trigger; and wherein the drive actuator has a predetermined thickness and the drive actuator includes a relieved section having a reduced thickness located adjacent the curved portion of the support member to permit the drive actuator to bend as it moves through the curved portion of the support member.

12. The surgical instrument of claim 11, wherein relieved section includes a plurality of spaced apart ribs having substantially the predetermined thickness to position the relieved section of the drive actuator in the slot of the support member.

13. A surgical instrument comprising;

a handle including a movable trigger;

an elongated support member having a proximal end coupled to the handle and a distal end for insertion into a patient's body, the elongated support member including a curved portion located in close proximity to the distal end, the elongated support member being formed to include a slot extending from the proximal end to the distal end;

an operating unit coupled to the distal end of the support member;

a drive actuator configured to be positioned in the slot of the support member, the drive actuator having a distal end and a proximal end, the distal end of the drive actuator being coupled to the operating unit and the proximal end of the drive actuator being configured to engage the trigger so that the drive actuator moves the operating unit relative to the support member in response to movement of the trigger;

wherein a proximal end of the support member is inserted into a slot formed in the handle to couple the support member to the handle, and further comprising a locking mechanism for removably coupling the support member to the handle; and wherein the releasable locking mechanism includes a semi-cylindrical member for engaging a notch formed in the support member to secure the support member to the handle and means coupled to the semi-cylindrical member for rotating the semi-cylindrical member to release the support member from the handle.

14. A surgical instrument comprising:

a handle including a movable trigger;

an elongated support member having a proximal end coupled to the handle and a distal end for insertion into a patient's body;

an operating unit pivotably coupled to the distal end of the support member;

a drive actuator having a distal end and a proximal end, the proximal end of the drive actuator being configured to engage a portion of the movable trigger, and the distal end of the drive actuator being pivotably coupled to the operating unit for moving the operating unit relative to the support member in response to movement of the trigger;

in addition to the pivotal connection, a first stop formed on the operating unit to prevent disengagement of the distal end of the drive actuator from the operating unit; and a second stop formed on the support member to prevent disengagement of the operating unit from the support member.

15. The surgical instrument of claim 14, further comprising a locking member for removably coupling the proximal end of the drive actuator to the handle, the locking member being movable from a first position to hold the drive actuator in a locked position relative to the handle to a second position to release the drive actuator from the handle and to permit movement of the drive actuator away from the handle to permit cleaning, sterilization, and inspection of the support member, the drive actuator, and the operating unit after a surgical procedure.

16. The surgical instrument of claim 14, wherein a proximal end of the support member is inserted into a slot formed in the handle to couple the support member to the handle, and further comprising a locking mechanism for removably coupling the support member to the handle.

17. The surgical instrument of claim 16, wherein the releasable locking mechanism includes a semi-cylindrical member for engaging a notch formed in the support member to secure the support member to the handle and means coupled to the semi-cylindrical member for rotating the semi-cylindrical member to release the support member from the handle.

18. The surgical instrument of claim 14, wherein the drive actuator includes a projection extending outwardly therefrom and the operating unit is formed to include a notch therein for receiving the projection therein to pivotably couple the drive actuator to the operating unit.

19. The surgical instrument of claim 14, wherein the operating unit is coupled to the support member by an arcuate groove and notch arrangement to couple the operating unit to the support member.

20. The surgical instrument of claim 14, wherein the support member is formed to include a trough-like slot having a generally U-shaped transverse cross section, the drive actuator is configured to be disposed at least partially within the trough-like slot.

21. The surgical instrument of claim 20, wherein the trough-like slot and the drive actuator define a passage therebetween for receiving at least one of an illumination, optical, irrigation, suction, and laser line therein.

22. The surgical instrument of claim 14, wherein the support member is formed to include a curved portion located in close proximity to the distal end and a slot extending from the proximal end to the distal end of the support member for receiving the drive actuator therein.

23. The surgical instrument of claim 22, wherein the drive actuator has a predetermined thickness and includes a relieved section having a reduced thickness located adjacent the curved portion of the support member to permit the drive actuator to bend as it moves through the curved portion of the support member.

24. The surgical instrument of claim 23, wherein relieved section includes a plurality of spaced apart ribs.

25. A surgical instrument kit comprising:

a first removable tip assembly including a straight support member having a proximal end configured to be coupled to a handle and a distal end for insertion into a patient's body, the distal end of the support member being coupled to an operating unit by an arcuate groove and notch arrangement;

a second removable tip assembly including a curved support member having a proximal end configured to be coupled to the handle and a distal end for insertion into the patient's body, the distal end of the curved support member being coupled to an operating unit by an arcuate groove and notch arrangement; and a handle having a body portion configured to receive the proximal end of a selected one of the first and second tip assemblies therein, a movable trigger connectable to actuate the operating unit of the selected tip assembly, and a locking mechanism for removably coupling the selected tip assembly to the handle, the locking mechanism being movable from a first position to hold the selected tip assembly in a locked position relative to the handle to a second position to release the selected tip assembly from the handle and permit the removal of the selected tip assembly from the handle.

26. A surgical instrument comprising:

a removable tip assembly including an elongated support member having a proximal end configured to be coupled to a handle and a distal end for insertion into a patient's body, an operating unit coupled to the distal end of the support member, and a drive actuator having a distal end and a proximal end, the distal end of the drive actuator being pivotably coupled to the operating unit for moving the operating unit relative to the support member;

a handle having a body portion formed to include an opening for slidably receiving the proximal end of the tip assembly therein, a movable trigger connectable to actuate the operating unit of the tip assembly, and a locking mechanism for removably coupling the tip assembly to the handle, the locking mechanism being movable from a first position to hold the tip assembly in a locked position relative to the handle to a second position to release the tip assembly from the handle and permit the removal of the tip assembly from the handle; and wherein the releasable locking mechanism includes a semi-cylindrical member for engaging a notch formed in the support member to secure the support member to the handle and means coupled to the semi-cylindrical member for rotating the semi-cylindrical member to release the support member from the handle.

27. A surgical instrument comprising;

a removable tip assembly including an elongated support member having a proximal end configured to be coupled to a handle and a distal end for insertion into a patient's body, an operating unit coupled to the distal end of the support member, and a drive actuator having a distal end and a proximal end, the distal end of the drive actuator being pivotably coupled to the operating unit for moving the operating unit relative to the support member;

a handle having a body portion formed to include an opening for slidably receiving the proximal end of the tip assembly therein, a movable trigger connectable to actuate the operating unit of the tip assembly and a locking mechanism for removably coupling the tip assembly to the handle, the locking mechanism being movable from a first position to hold the tip assembly in a locked position relative to the handle to a second position to release the tip assembly from the handle and permit the removal of the tip assembly from the handle; and wherein the support member is formed to include a curved portion located in close proximity to the distal end and an open trough slot extending from the proximal end to the distal end of the support member for receiving the drive actuator therein.

28. The surgical instrument of claim 27, wherein the drive actuator has a predetermined thickness and includes a relieved section having a reduced thickness located adjacent the curved portion of the support member to permit the drive actuator to bend as it moves through the curved portion of the support member.

29. The surgical instrument of claim 28, wherein relieved section includes a plurality of spaced apart ribs.

30. A surgical instrument comprising:

a removable tip assembly including an elongated support member having a proximal end configured to be coupled to a handle and a distal end for insertion into a patient's body, an operating unit coupled to the distal end of the support member, and a drive actuator having a distal end and a proximal end, the distal end of the drive actuator being pivotably coupled to the operating unit for moving the operating unit relative to the support member;

a handle having a body portion formed to include an opening for slidably receiving the proximal end of the tip assembly therein, a movable trigger connectable to actuate the operating unit of the tip assembly, and a locking mechanism for removably coupling the tip assembly to the handle, the locking mechanism being movable from a first position to hold the tip assembly in a locked position relative to the handle to a second position to release the tip assembly from the handle and permit the removal of the tip assembly from the handle; and wherein the body portion of the handle is formed to include first and second elongated tracks in the opening for engaging first and second notched sections formed in the proximal end of the support member to align the support member relative to the body portion and to prevent rotation of the support member relative to the body portion.

31. The surgical instrument of claim 30, wherein body portion of the handle is formed to include a slot therein for receiving the proximal end of the drive actuator, and the first and second tracks are aligned downwardly away from the slot in the body portion of the handle at a predetermined angle to prevent spreading of the body portion of the handle due to a prying force on the tip assembly.

32. The surgical instrument of claim 31, wherein the predetermined angle is about 6° to about 10°.

33. A surgical instrument comprising:

a removable tip assembly including an elongated support member having a proximal end configured to be coupled to a handle and a distal end for insertion into a patient's body;

an operating unit coupled to the distal end of the support member using an arcuate groove and follower connection wherein the groove is located on one of the operating unit and support member and the follower is located on the other of the operating unit and support member and wherein the follower rides in the groove;

a drive actuator having a distal end and a proximal end, the distal end of the drive actuator being releasably and pivotably coupled to the operating unit for moving the operating unit relative to the support member through a notch and projection connection wherein the drive actuator can be disconnected from the moveable trigger to be pivoted with respect to the operating unit to a point where the projection can be released from the notch; and a handle having a body portion formed to include an opening for releasably receiving the proximal end of the tip assembly therein and a movable trigger connectable to actuate the proximal end of the drive actuator.

34. The surgical instrument of claim 33, further comprising a locking member for removably coupling the proximal end of the drive actuator to the handle, the locking member being movable from a first position to held the drive actuator in a locked position relative to the handle to a second position to release the drive actuator from the handle and to permit movement of the drive actuator away from the handle to permit cleaning, sterilization, and inspection of the support member, the drive actuator, and the operating unit after surgical procedure.

35. The surgical instrument of claim 33, wherein the projection is located adjacent the distal end of the drive actuator and includes an elongated member for engaging the notch, which notch is formed in the operating unit.

* * * * *